(12) United States Patent
Warkentin et al.

(10) Patent No.: US 9,149,638 B2
(45) Date of Patent: Oct. 6, 2015

(54) METHOD AND SYSTEM FOR CONTROLLING PULMONARY CAPILLARY PRESSURE

(75) Inventors: Dwight H. Warkentin, Arden Hills, MN (US); David E. Euler, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 3020 days.

(21) Appl. No.: 11/343,175

(22) Filed: Jan. 30, 2006

(65) Prior Publication Data
US 2007/0179545 A1    Aug. 2, 2007

(51) Int. Cl.
*A61N 1/36* (2006.01)
*A61N 1/362* (2006.01)
*A61N 1/365* (2006.01)

(52) U.S. Cl.
CPC .......... *A61N 1/3627* (2013.01); *A61N 1/36564* (2013.01)

(58) Field of Classification Search
USPC ........................................... 607/9, 18, 27, 28
See application file for complete search history.

(56) References Cited

U.S. PATENT DOCUMENTS

| | | | |
|---|---|---|---|
| 5,213,098 A * | 5/1993 | Bennett et al. ................. | 607/18 |
| 6,438,408 B1 | 8/2002 | Mulligan et al. | |
| 6,463,324 B1 * | 10/2002 | Ben-Haim et al. ................ | 607/9 |
| 6,587,721 B1 * | 7/2003 | Prutchi et al. ..................... | 607/9 |
| 6,738,667 B2 | 5/2004 | Deno et al. | |
| 2002/0115939 A1 | 8/2002 | Mulligan et al. | |
| 2003/0074029 A1 | 4/2003 | Deno et al. | |
| 2004/0049235 A1 | 3/2004 | Deno et al. | |
| 2004/0147969 A1 | 7/2004 | Mann et al. | |
| 2004/0220631 A1 | 11/2004 | Burnes et al. | |
| 2004/0220640 A1 * | 11/2004 | Burnes et al. ................... | 607/28 |
| 2005/0075673 A1 | 4/2005 | Warkentin et al. | |
| 2005/0075674 A1 | 4/2005 | Zillmer et al. | |
| 2005/0075675 A1 | 4/2005 | Mulligan et al. | |
| 2005/0075676 A1 | 4/2005 | Deno et al. | |
| 2005/0090872 A1 | 4/2005 | Deno et al. | |
| 2005/0101998 A1 | 5/2005 | Kleckner et al. | |

FOREIGN PATENT DOCUMENTS

| | | | | |
|---|---|---|---|---|
| WO | WO 98/10832 | * | 3/1998 | ............. A61N 1/362 |
| WO | WO 0158518 | * | 8/2001 | |
| WO | WO 03/037428 | | 5/2003 | |

OTHER PUBLICATIONS

PCT International Search report, PCT/US07/061059, 4 pages.

* cited by examiner

*Primary Examiner* — Carl H Layno
*Assistant Examiner* — Ankit Tejani
(74) *Attorney, Agent, or Firm* — Carol F. Barry

(57) ABSTRACT

A method of controlling pulmonary capillary pressure is disclosed which includes increasing the output of a first ventricle (V1) (e.g., a left ventricle) relative to second ventricle (e.g., right ventricle) by increasing the magnitude of a post extrasystolic potentiation (PESP) therapy effect in the first ventricle relative to the magnitude of a PESP therapy effect produced in the second ventricle. In certain embodiments of the invention, this may be accomplished by adjusting the extra-stimulus interval (ESI) in either or both of the left ventricle and the right ventricle, for example.

31 Claims, 7 Drawing Sheets

FIG. 6

| | Right Ventricle | | Left Ventricle | |
|---|---|---|---|---|
| | Initial State | Final State | Initial State | Final State |
| (a) | No Premature Stimulation | No Premature Stimulation | No Premature Stimulation | Premature Stimulation |
| (b) | Premature Stimulation | No Premature Stimulation | Premature Stimulation | Premature Stimulation |
| (c) | Premature $Stim_{ESI-RV}$ | Premature $Stim_{ESI-RV}$ | Premature $Stim_{ESI-LV}$ | Premature $Stim_{ESI-LV}^{--}$ |
| (d) | Premature $Stim_{ESI-RV}$ | Premature $Stim_{ESI-RV}^{++}$ | Premature $Stim_{ESI-LV}$ | Premature $Stim_{ESI-LV}$ |

FIG. 7

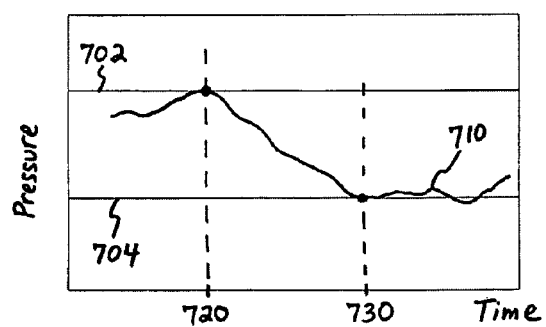

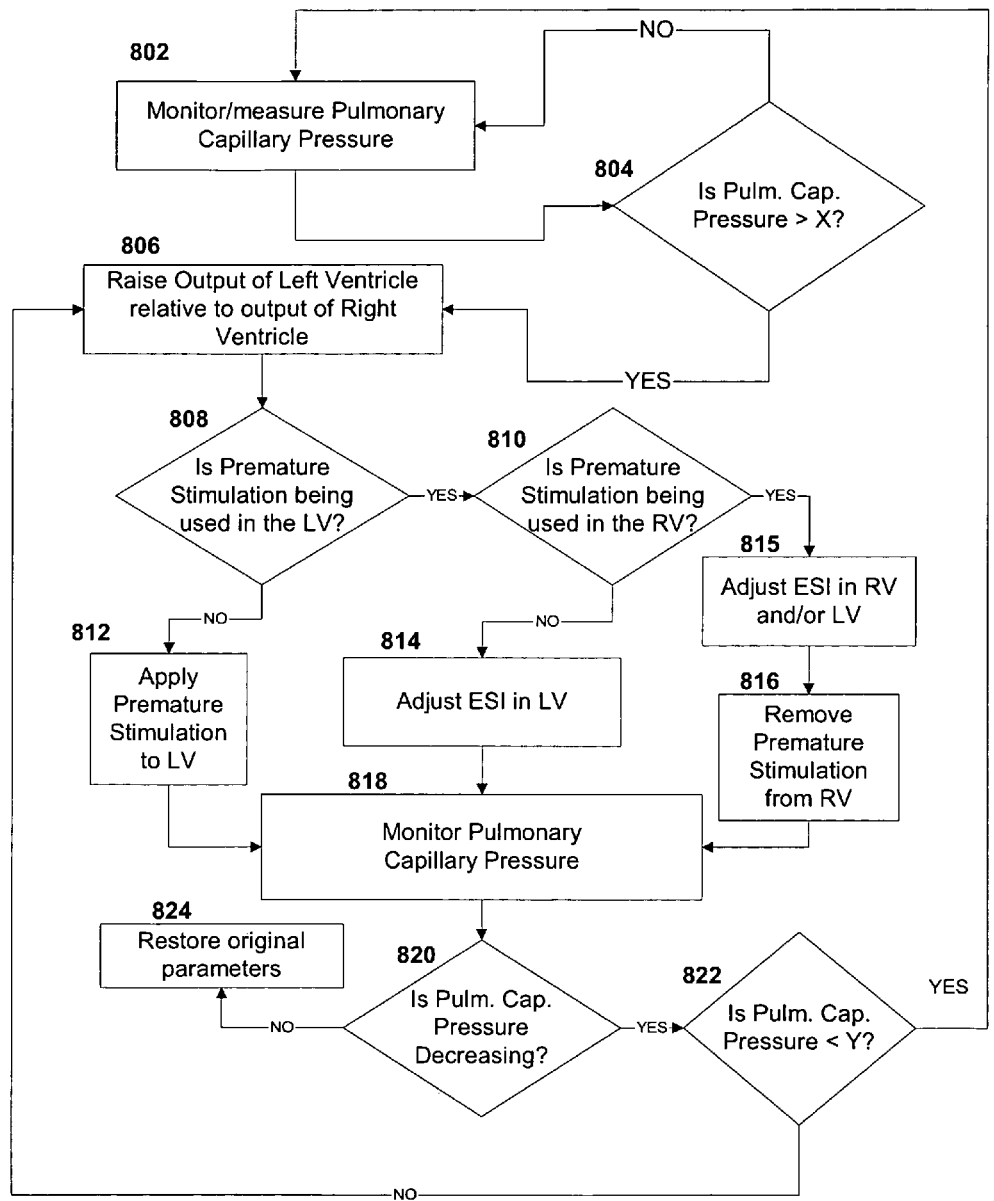

METHOD AND SYSTEM FOR CONTROLLING PULMONARY CAPILLARY PRESSURE

FIELD

Most of the disclosure relates generally to a method of using post extrasystolic potentiation (PESP) therapy to control pulmonary capillary pressure, and more particularly, to a method of independently varying PESP between the right and left ventricles to control pulmonary capillary pressure.

BACKGROUND

Pulmonary congestion (pulmonary edema) is the accumulation of fluid in the pulmonary tissues and air spaces in the lungs of a patient due to changes in hydrostatic forces in the capillaries. Pulmonary edema may be caused by increased pulmonary capillary hydrostatic pressure. A patient with pulmonary edema may experience shortness of breath and difficulty breathing.

PESP is a pacing therapy for improving cardiac function that used paired- or coupled pacing of a cardiac chamber. PESP is a property of cardiac cells whereby a pair of closely-spaced depolarizations of a heart chamber results in subsequent contractions that are of an increased magnitude.

PESP may be employed by supplying an "extra" pacing stimulus, delivered shortly after an intrinsic (or paced) depolarization event, which causes a second depolarization without a corresponding mechanical contraction. The time interval between the initial depolarization event and the extra pacing stimulus is called the extra stimulus interval, or ESI. In general, the shorter the ESI, the greater the magnitude of the PESP effect.

SUMMARY OF THE INVENTION

In certain embodiments of the invention, a method of reducing pulmonary capillary pressure is disclosed which includes independently controlling the magnitude of the PESP effect between the right and left ventricles. In certain embodiments, the magnitude of the PESP effect for a given chamber of the heart (e.g., the left ventricle) may be varied by varying the length of the extra stimulus interval (ESI) in that chamber.

DESCRIPTION OF THE DRAWINGS

FIG. 6 is a table showing a method for controlling pulmonary capillary pressure in accordance with embodiments of the invention;

FIG. 7 is a plot of pulmonary capillary pressure being reduced in accordance with embodiments of the invention; and FIG. 8 is a flow chart describing a method for controlling pulmonary capillary pressure in accordance with embodiments of the invention.

DETAILED DESCRIPTION

Figure 1:
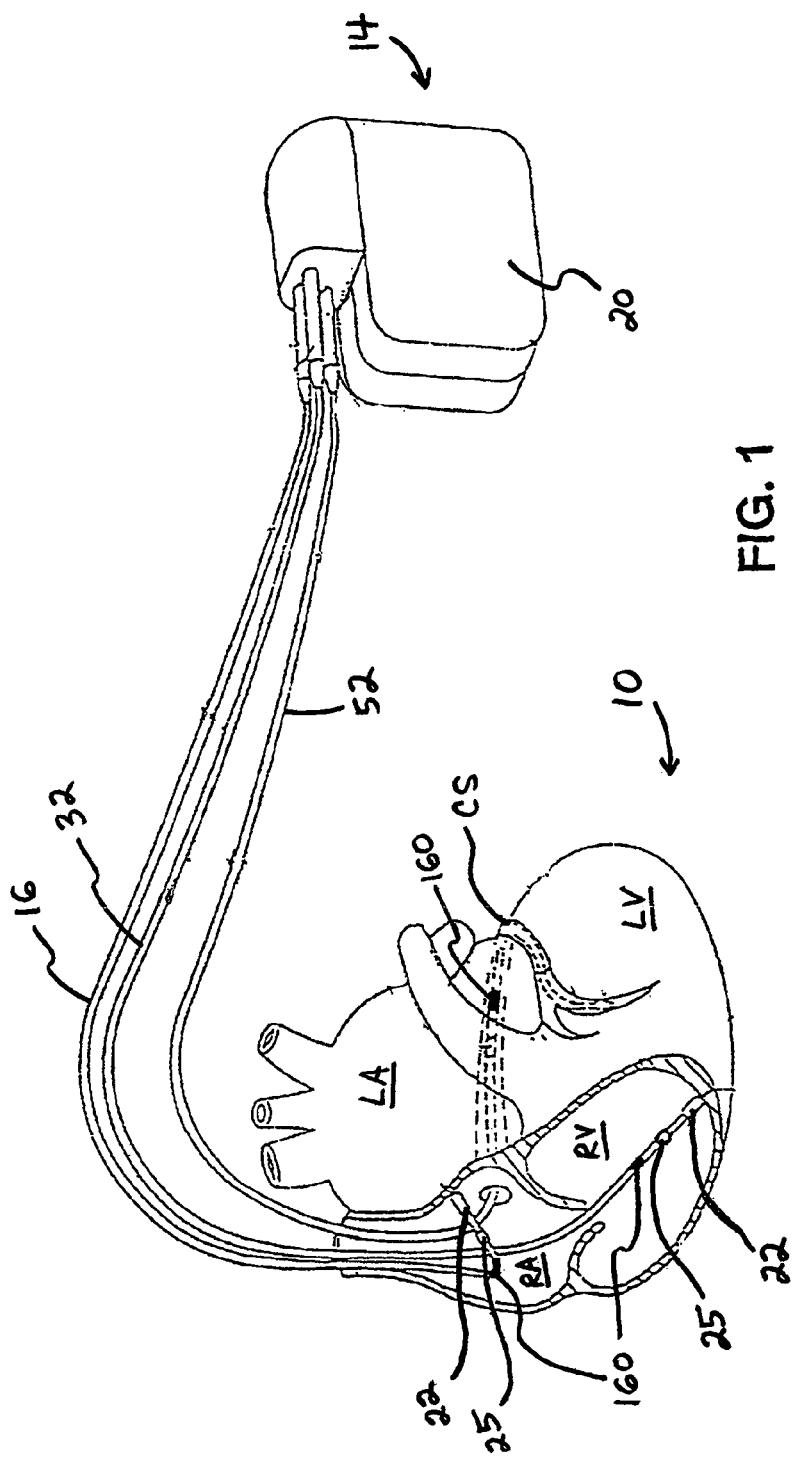
FIG. 1 is a schematic diagram depicting a multi-channel, atrial and bi-ventricular, monitoring/pacing implantable medical device (IMD) in which embodiments of the invention may be implemented.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Post-extra systolic potentiation (PESP) is a property of cardiac myocytes that results in enhanced mechanical function of the heart on the beats following an extra stimulus delivered early after the refractory period of either an intrinsic or pacing-induced systole. The magnitude of the enhanced mechanical function is dependent on the timing of the extra systole produced by the extra stimulus relative to the preceding intrinsic or paced systole. The magnitude of PESP may be maximized by delivering a stimulus immediately following the refractory period of an intrinsic or pacing-induced systole, and may attenuate as the stimulus is delivered later in the cardiac cycle. When correctly timed, an extra stimulus pulse may cause an electrical depolarization of the heart, but the attendant mechanical contraction is absent or substantially weakened. The contractility of the subsequent cardiac cycles, referred to as the post-extra systolic beats, is thereby increased.

As noted, the degree of mechanical augmentation on post-extra systolic beats depends on the timing of the extra systole following a first depolarization, referred to as the extra systolic interval (ESI). If the ESI is too long, the PESP effect is not achieved because a normal mechanical contraction takes place in response to the extra stimulus. As the ESI is shortened, a maximal effect may be reached when the ESI is slightly longer than the electrical (or effective) refractory period. A properly timed extra stimulus results in electrical depolarization occurring without an attendant mechanical contraction, or with a substantially weakened contraction. If the ESI becomes too short, the extra stimulus falls within the absolute refractory period and no depolarization occurs.

PESP stimulation may be employed to strengthen the cardiac contraction, and may enable a patient to benefit from increased myocardial contractility and increased cardiac output. Certain embodiments of the invention may include, or may be adapted for use in implantable medical devices (IMDs), including implantable hemodynamic monitors (IHMs), implantable cardioverter-defibrillators (ICDs), cardiac pacemakers, cardiac resynchronization therapy (CRT) pacing devices, drug delivery devices, or combinations of such devices.

FIG. 1 is a schematic representation of an implantable medical device (IMD) 14 that may be used in accordance with certain embodiments of the invention. The IMD 14 may be any device that is capable of measuring hemodynamic parameters (e.g., blood pressure signals) from within a ventricle of a patient's heart, and which may further be capable of measuring other signals, such as the patient's electrogram (EGM).

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes.

It should be noted that the IMD 14 may also comprise an ICD, a CRT device, an IHM, or any other such device or combination of devices (e.g., a neurostimulator, a drug pump, etc.) according to various embodiments of the invention.

Typically, in pacing systems of the type illustrated in FIG. 1, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors.

In addition, some or all of the leads shown in FIG. 1 could carry one or more pressure sensors for measuring systolic and diastolic pressures, and a series of spaced apart impedance sensing leads for deriving volumetric measurements of the expansion and contraction of the RA, LA, RV and LV. In some embodiments, some or all of the leads shown in FIG. 1 could further include ECG or electrogram (EGM) sensors (e.g., on the can electrode 20) to measure changes in the ST segments of the ECG, which may enable changes in ischemia and/or coronary perfusion to be measured.

The leads and circuitry described above can be employed to record EGM signals, blood pressure signals, and impedance values over certain time intervals. The recorded data may be periodically telemetered out to a programmer operated by a physician or other healthcare worker in an uplink telemetry transmission during a telemetry session, for example.

Figure 2:
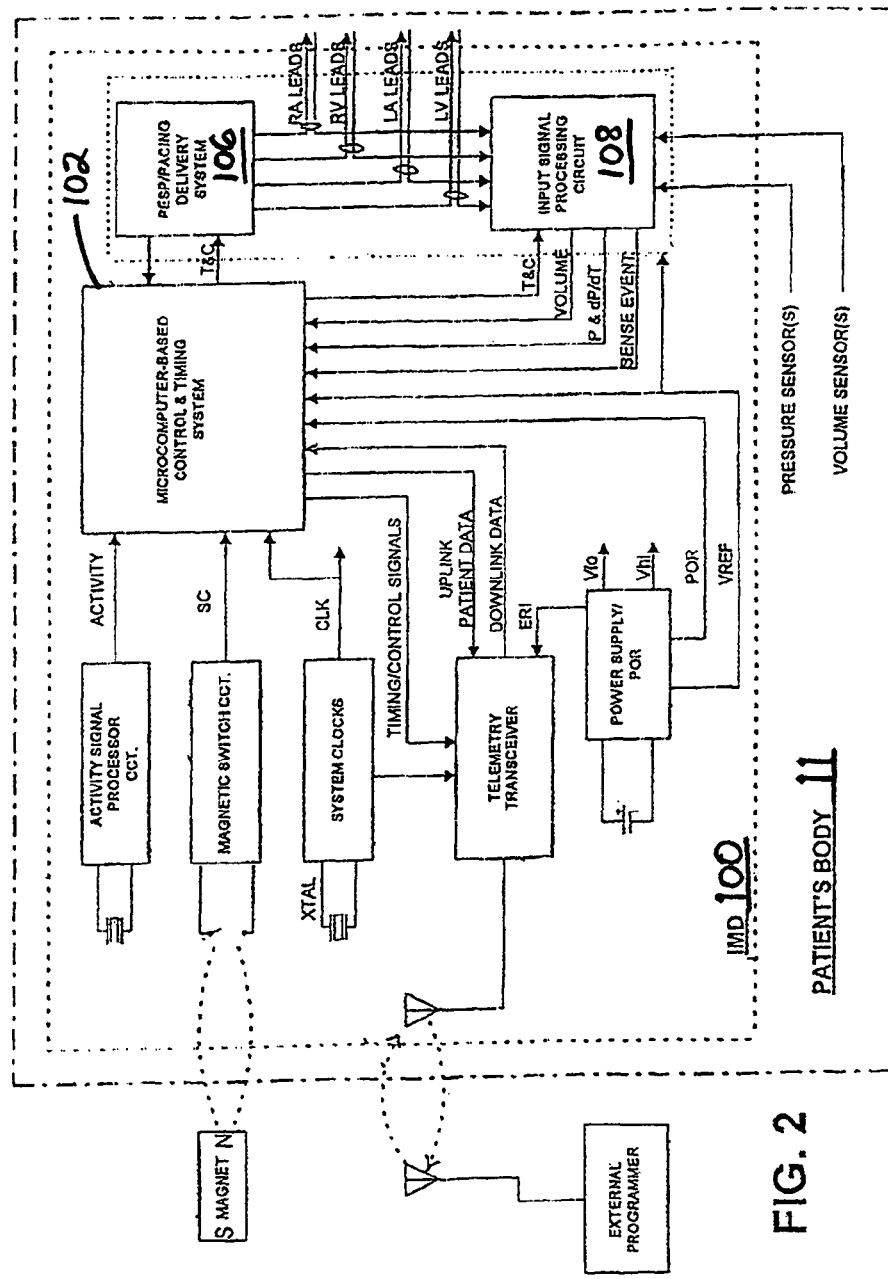
FIG. 2 is a simplified block diagram of an embodiment of IMD circuitry and associated leads that may be employed in the system of FIG. 1 to enable selective therapy delivery and monitoring in one or more heart chambers.

FIG. 2 depicts a system architecture of an exemplary multi-chamber monitor/sensor 100 implanted into a patient's body 11 that provides delivery of a therapy and/or physiologic input signal processing. The typical multi-chamber monitor/sensor 100 has a system architecture that is constructed about a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart to alleviate heart failure, or to operate an implantable heart assist device or pump (including balloon pumps) implanted in patients (e.g., patients having acute heart failure and/or cardiogenic shock), or in patients awaiting a heart transplant operation, or as a bridge to recovery. Alternately, the therapy delivery system 106 may be configured as an ultra-filtration device to unload the heart or assist in renal function.

The input signal processing circuit 108 includes at least one physiologic sensor signal processing channel for sensing and processing a sensor derived signal from a physiologic sensor located in relation to a heart chamber or elsewhere in the body. Examples illustrated in FIG. 2 include pressure and volume sensors, but could include other physiologic or hemodynamic sensors.

Figure 3:
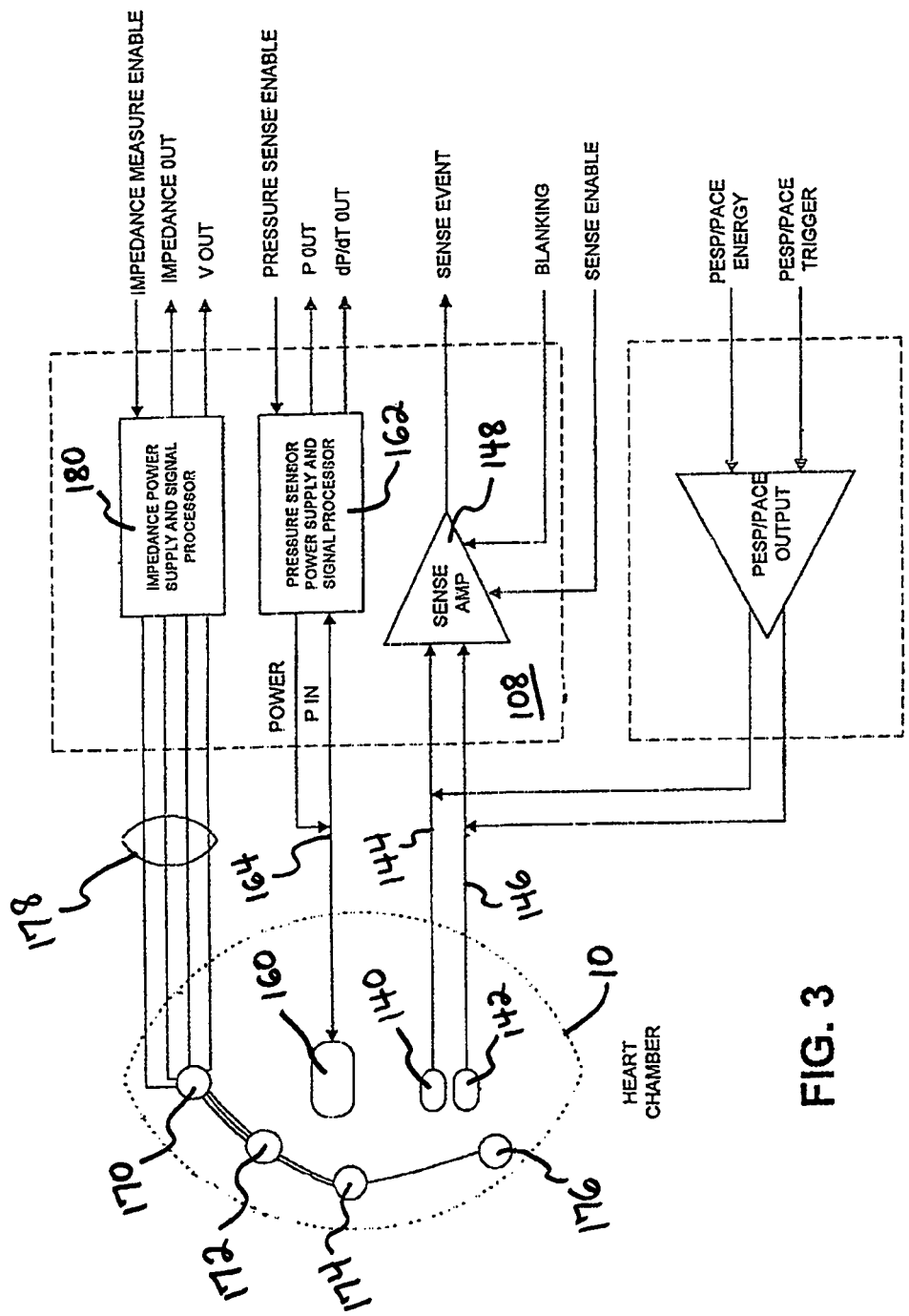
FIG. 3 is a simplified block diagram of a single monitoring and pacing channel for acquiring pressure, impedance and cardiac EGM signals employed in monitoring cardiac function and/or delivering therapy, including pacing therapy, in accordance with embodiments of the invention.

FIG. 3 schematically illustrates one pacing, sensing and parameter measuring channel in relation to one heart chamber. A pair of pace/sense electrodes 140, 142, a pressure sensor 160, and a plurality, e.g., four, impedance measuring electrodes 170, 172, 174, 176 are located in operative relation to the heart 10.

The pair of pace/sense electrodes 140, 142 are located in operative relation to the heart 10 and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled in a manner known in the pacing art. The blanking signal is provided by control and timing system 102 upon delivery of a pacing or PESP pulse or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM. The control and timing system responds to non-refractory sense events by restarting an escape interval (EI) timer timing out the EI for the heart chamber, in a manner well known in the pacing art.

The pressure sensor 160 is coupled to a pressure sensor power supply and signal processor 162 within the input signal processing circuit 108 through a set of lead conductors 164. Lead conductors 164 convey power to the pressure sensor 160, and convey sampled blood pressure signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure (P), developed pressure (DP) and pressure rate of change (dP/dt) sample values can be developed by the pressure sensor power supply and signal processor 162 or by the control and timing system 102 for storage and processing.

A variety of hemodynamic parameters may be recorded, for example, including right ventricular (RV) systolic and diastolic pressures (RVSP and RVDP), estimated pulmonary artery diastolic pressure (ePAD), pressure changes with respect to time (dP/dt), heart rate, activity, and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

The data stored by IMD 14 may include continuous monitoring of various parameters, for example recording intracardiac EGM data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may, for example, contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256 Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

Hemodynamic parameters that may be used in accordance with various embodiments of the invention include parameters that are directly measured, such as RVDP and RVSP, as well as parameters that may be derived from other pressure parameters, such as estimated pulmonary artery diastolic pressure (ePAD), rate of pressure change (dP/dt), etc.

In certain embodiments of the invention, the data stored by IMD 14 may further include information regarding sympathetic activity, for example, via monitoring of nerve traffic. Sympathetic activity may, for example, be monitored through use of a nerve cuff electrode adapted to monitor sympathetic activity of the peroneal nerve.

Figure 4:
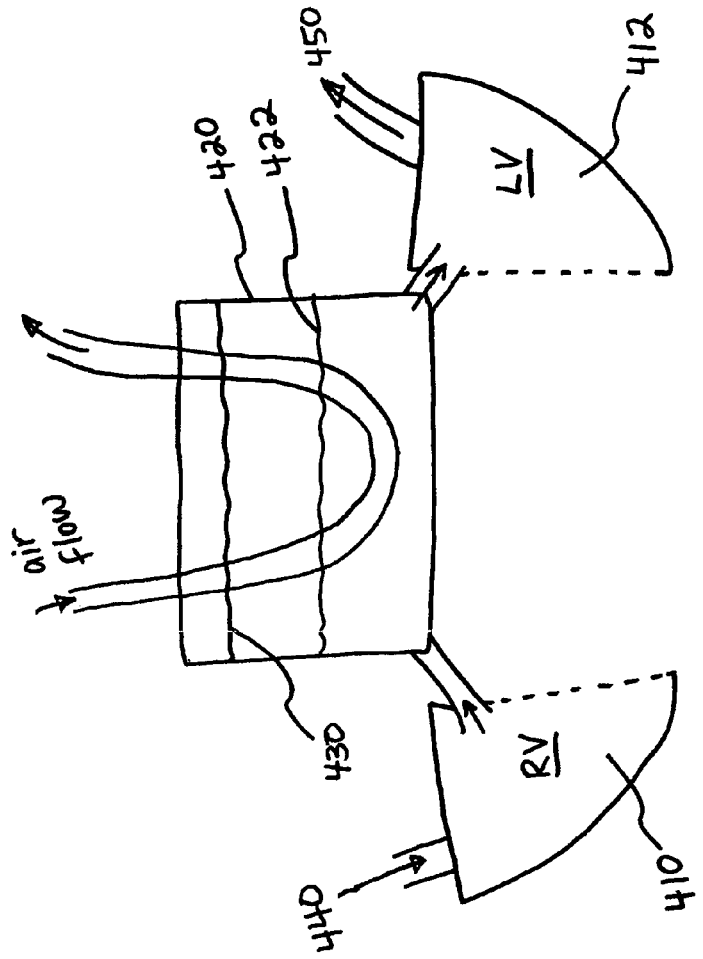
FIG. 4 is a simplified conceptual illustration of the cardiopulmonary system.

FIG. 4 conceptually illustrates the cardiopulmonary system, showing venous return blood 440 flowing into the right ventricle (RV) 410, pulmonary blood flow from the RV 410 to the lungs 420, oxygenated blood flow from the lungs 420 to the left ventricle (LV) 412, and from the LV 412 to the aorta to supply oxygenated blood 450 to the body. Also shown is air flow to and from the lungs 420. Pulmonary congestion or edema is shown in FIG. 4 as a build-up of fluid in the lungs, as illustrated by the elevation in fluid level from an initial level 422 to an elevated level 430, which may also manifest as elevated pulmonary capillary pressure.

Elevated pulmonary capillary pressure, which may be indicative of pulmonary congestion or edema, may be reduced by at least temporarily increasing the LV output (e.g., by increasing the LV stroke volume) above that of the RV according to certain embodiments of the invention. A transient LV output that is greater than the RV output should tend to reduce pulmonary capillary pressure and thereby decrease the likelihood or onset of pulmonary congestion or edema. LV output may be increased relative to RV output by using PESP therapy in some embodiments of the invention. PESP therapy is an excitatory stimulation therapy which aims to improve cardiac function. The PESP effect is observed when a pair of closely-spaced depolarizations of a heart chamber are followed by a subsequent contraction of the affected chamber of increased magnitude.

The magnitude of the PESP effect (i.e., the amount by which the contraction of the affected chamber is increased by PESP) may be controlled by adjusting the interval between the initial depolarization and a premature stimulus. The interval (termed the extra-stimulus interval or ESI) may be a coupling interval between an intrinsic depolarization and a premature stimulus (i.e., coupled pacing), or a paired pacing interval between a paced depolarization and a premature stimulus (i.e., paired pacing). By making the ESI shorter, the magnitude of the PESP effect may be increased. The PESP parameters may be adjusted so that the magnitude of the PESP effect in the left ventricle is at least temporarily greater than that in the right ventricle, for example, by shortening the ESI in the LV relative to the ESI in the RV. By increasing the magnitude of the PESP effect in the LV, LV output may be increased relative to RV output, and pulmonary capillary pressure may thereby be reduced. It should be noted that the magnitude of the PESP effect may include a "zero" condition in which no extra pacing stimulus is delivered. Thus, an increase in the magnitude of the PESP effect may be caused by simply changing from such a "zero" condition to one in which an extra stimulus is applied.

FIGS. 5-8 illustrate the use of PESP to augment the mechanical contraction of a given heart chamber (e.g., the LV) to thereby control pulmonary capillary pressure.

Figure 5:
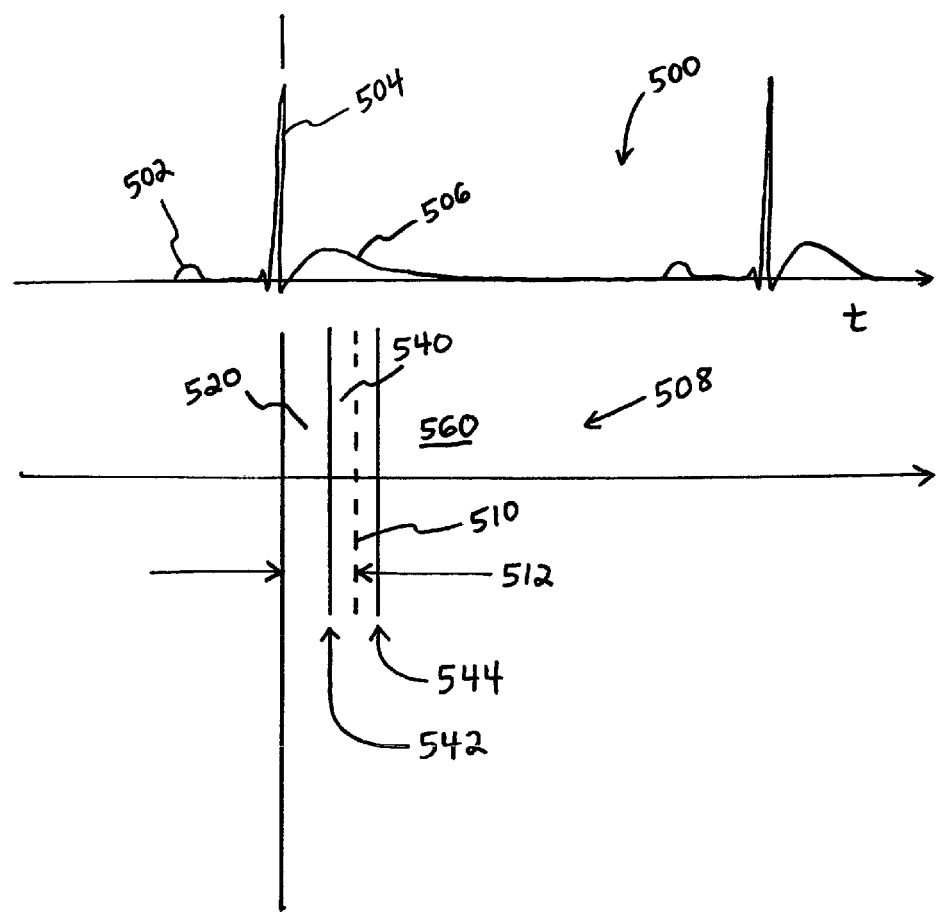
FIG. 5 is a timing diagram showing timing relationships between electrocardiogram (ECG) signals and extra-stimulus intervals (ESI's)

FIG. 5 is a timing diagram that illustrates the use of PESP generally, showing the timing of extra stimulus pulses relative to a cardiac cycle. For example, FIG. 5 shows a typical ECG signal 500, having a P-wave 502, an R-wave 504, and a T-wave 506. A time plot 508 is illustrated beneath ECG signal 500 showing timing zones that correspond generally to different responses to an applied extra pacing stimulus in a ventricle following a ventricular depolarization. Similar timing zones may exist following an atrial depolarization, but are not illustrated here for simplicity. A first zone 520 immediately following R-wave 504 and continuing until time 542 represents an electrical (or effective) refractory period during which a premature stimulus does not cause a second or subsequent depolarization of the cardiac cells.

A second zone 540 following first zone 520 (from time 542 to time 544) represents a period during which a premature stimulus may cause a second or subsequent depolarization of the affected myocardial tissue without an attendant mechanical contraction. A premature stimulus (or extra stimulus) applied during zone 540 may cause the PESP effect to be observed (e.g., by an enhanced or augmented contraction on subsequent cardiac cycles). The magnitude of the PESP effect tends to be greater when the extra stimulus is applied nearer the beginning of zone 540 (i.e., closer to time 542), and tends to decrease as the extra stimulus occurs later in zone 540 (i.e., closer to time 544).

FIG. 5 illustrates the timing of an extra stimulus interval (ESI) 512 that may result in the PESP effect. For example, the delivery of an extra stimulus (i.e., a pacing pulse) at time 510, corresponding to an ESI 512 after R-wave 504, may cause an enhanced or augmented contraction of the affected heart chamber on subsequent cardiac cycles. The magnitude of the resultant PESP effect may be increased by moving the timing 510 of the extra stimulus closer to time 542, or may be decreased by moving the timing 510 closer to time 544, for example. In some embodiments, the PESP effect may be reduced to zero by omitting the extra stimulus. For example, in certain embodiments, increasing the magnitude of the PESP effect in the LV relative to the magnitude of the PESP effect in the RV may include initiating PESP (to cause the PESP effect) in the LV when previously not employed, and may also include terminating PESP (to remove the PESP effect) in the RV when previously employed.

A third zone 560 follows zone 540, representing a period during which a premature stimulus may cause both a depolarization and a mechanical contraction of the affected myocardial tissue. The PESP effect may not be observed when an extra stimulus falls in zone 560, since both a depolarization and an attendant contraction will occur.

It should be noted that the timing and duration of zones 520, 540, and 560 in FIG. 5 relative to ECG 500 are for illustrative purposes only. The timing and duration of these zones may vary between the right and left ventricles, and may also be different for the atria, and may further vary as a function of time, activity and heart rate.

FIG. 6 is a table showing a number of steps that may be taken to control pulmonary capillary pressure in accordance with embodiments of the invention. For example, step (a) in FIG. 6 may be taken to increase the left ventricular output relative to the right ventricular output when there is no premature stimulation therapy delivery to begin with, and hence, no PESP effect in either ventricle. In step (a), premature stimulation therapy delivery is applied to the left ventricle when it was not previously enabled to achieve greater PESP in the left ventricle than in the right ventricle.

It should be noted that premature stimulation therapy delivered in one chamber only (e.g., the delivery of an extra stimulus in the LV but not the RV) may cause a depolarization (extra-systole) that will propagate from the LV to the RV, producing a PESP effect in both chambers. However, since it takes time (typically 100-200 msec) for a cardiac impulse to conduct from the left side to the right side (or vice versa), the effective ESI in the RV may be longer than in the LV and there may be less PESP effect in the RV than the LV as a result. The reverse situation may occur when an extra stimulus is delivered only in the RV.

As is known, premature stimulation therapy delivery may include both coupled pacing, as well as paired pacing, in accordance with certain embodiments of the invention. For example, paired pacing may be employed if the patient's intrinsic rate drops below a predetermined lower rate limit. As noted above with reference to FIG. 5, the PESP effect may be accomplished by the application of an extra stimulus after an intrinsic depolarization (i.e., coupled pacing), or after a paced depolarization (i.e., paired pacing), and timed to cause a second or subsequent depolarization without an attendant mechanical contraction.

Step (b) in FIG. 6 describes a different situation from step (a), wherein premature stimulation therapy is being delivered in both the right and left ventricular chambers to begin with. In step (b), the delivery of premature stimulation therapy in the right ventricle is removed. As a result, the extra systole in the LV may conduct to the RV with an intrinsic delay of about 100-200 msec, resulting in a longer ESI in the RV, and thus, less PESP effect in the RV than in the LV. The result of step (b) should, as with step (a), result in more left ventricular output (e.g., stroke volume) relative to right ventricular output, but step (b) does so by reducing the right ventricular output rather than increasing the left ventricular output.

It should be noted that the actions taken in steps (a) and (b) could be combined to achieve similar results. For example, the addition of premature stimulation therapy delivery in the left ventricle concurrently or in sequence with the removal of premature stimulation therapy delivery from the right ventricle may provide an increase in left ventricular output relative to right ventricular output, given the necessary initial conditions (e.g., premature stimulation therapy delivery disabled in the left ventricle and enabled in the right ventricle).

Step (c) in FIG. 6 describes an action that may be taken to increase left ventricular output relative to right ventricular output where premature stimulation therapy is delivered to both chambers, both before and after step (c). The net effect of step (c) may be to decrease the extra stimulus interval (ESI) in the left ventricle to thereby increase the magnitude of the PESP effect in the left ventricle. As noted previously with reference to FIG. 5, the ESI may be reduced within zone 540 (FIG. 5) to increase the magnitude of the PESP effect, which may increase the output of the affected heart chamber.

Step (d) in FIG. 6 attempts to reduce the right ventricular output relative to the left ventricular output by increasing the ESI of the right ventricle. As noted previously with reference to FIG. 5, increasing the ESI tends to cause a decrease in the magnitude of the PESP effect in the affected chamber, and should thereby result in reduced output from the affected chamber. It should be noted that steps (c) and (d) may be combined to achieve a similar result. For example, the ESI of the left ventricle may be decreased while simultaneously increasing the ESI of the right ventricle to obtain a potentially more pronounced increase in left ventricular output relative to right ventricular output.

It should also be noted that combinations of steps (a) through (d) may be employed to obtain an increase in LV output relative to RV output. For example, steps (b) and (c) may be performed together (concurrently or in sequence), as may steps (a) and (d), according to various embodiments of the invention. One of ordinary skill in the art would recognize that other combinations of steps may be possible, and would be deemed to fall within the scope of the invention as claimed. It should be further noted that steps (a) through (d) in FIG. 6 may be terminated (i.e., standard pacing or premature stimulation therapy delivery parameters returned to a prior or initial state) upon the end of an episode of high pulmonary capillary pressure, for example. Similarly, the pacing parameters may return to a prior or initial state upon completion of a predetermined period of time employing any of the steps (a) through (d) in FIG. 6.

There may be limits to the amount by which the ESI in the affected chamber can be either increased or decreased (e.g., in steps (c) and (d)) while maintaining the PESP effect. In other words, increasing or decreasing the ESI outside of zone 540 (FIG. 5) may cause the PESP effect in the affected chamber to diminish or be lost, for example. In certain embodiments, the extra-stimulus interval (ESI) in the LV may be decreased from a first ESI value between about 0-200 msec to a second ESI value between about 0-200 msec, the second ESI value being lower than the first ESI value. In some preferred embodiments, the ESI may range from about 10-80 msec, and more preferably, from about 10-30 msec.

FIG. 7 is a plot of pulmonary capillary pressure being controlled in accordance with certain embodiments of the invention. FIG. 7 shows pulmonary capillary pressure 710 plotted as a function of time during an episode in which pulmonary capillary pressure 710 reaches a predetermined high pressure setting 702, triggering a modification of PESP to reduce pulmonary capillary pressure 710. For example, pressure 710 may reach high pressure setting 702 at time 720, as indicated in FIG. 7 which may cause a pulmonary congestion episode to be detected according to certain embodiments of the invention. Beginning at time 720, one or more of the steps (a) through (d) described with reference to FIG. 6 may be applied to reduce pressure 710. The steps taken to reduce pressure 710 may be applied all at once (i.e., shortly after time 720), or may be applied and/or removed in a sequential or intermittent manner following time 720. In certain embodiments of the invention, the steps taken to reduce pressure 710 may continue for a predetermined period of time, then returned to their initial condition, according to certain embodiments of the invention (not shown). In some embodiments, the steps taken to reduce pressure 710 may continue until pressure 710 reaches pressure setting 704, indicating a normal or reduced pulmonary capillary pressure, thereby triggering the termination of the therapy steps taken to reduce pressure 710. In FIG. 7, pressure 710 is shown to have been reduced to pressure setting 704 at time 730, at which point the steps taken to reduce pressure 710 are returned to their initial condition, either all at once or sequentially according to some embodiments of the invention. Pressure 710 is shown to fluctuate after time 730, and is even shown dropping below pressure setting 704 temporarily.

In some embodiments, therapy steps such as those described above with respect to FIG. 6 may be delivered only to reduce pulmonary capillary pressure. In some embodiments, it may be additionally or alternatively desired to modify PESP parameters to increase pulmonary capillary pressure, for example, if pressure 710 drops below a predetermined low pressure setting (not shown in FIG. 7). One of ordinary skill in the art would recognize that the steps described with reference to FIG. 6 may be performed in the opposite direction (i.e., reversing the initial and final states shown in FIG. 6) to obtain an increase in pressure 710, if so desired.

With reference to FIG. 7, monitoring pressure 710 and comparing it to a high pressure setting 702 may further include measurement of a reference pressure to account for actual changes in absolute cardiac pressure prior to changing therapy parameters. Pressure 710 may rise or fall as a result of changes in altitude, such as elevator rides, driving up or down hills, and airplane travel, or with atmospheric pressure changes, for example without limitation. In certain embodiments of the invention, changes in hemodynamic pressures that are due to changes in altitude or changes in atmospheric pressure, for example, may be accounted for or compensated by providing an external pressure reference (EPR) signal that may be used to adjust the intracardiac pressure measured by an IMD/IHM. Such an EPR may, for example, be an implantable device or component, or may alternately be an external device kept or worn by a patient. An EPR, if used, may further have the ability to communicate reference pressure information to an IMD/IHM at periodic intervals. The EPR may function as a trending barometer and may, for example, make barometric pressure measurements periodically (e.g., once per minute). Data from an EPR may therefore be used to correct or compensate hemodynamic pressure data for changes in barometric pressure in accordance with certain embodiments of the invention.

FIG. 8 is a flow chart describing a method for controlling pulmonary capillary pressure in accordance with embodiments of the invention. Step 802 in FIG. 8 may be the starting point for a method of controlling pulmonary capillary pressure in accordance with certain embodiments of the invention. Pulmonary capillary pressure may be measured, estimated, or derived from measured hemodynamic pressure signals obtained from pressure sensors, for example, in accordance with embodiments of the invention. A derived hemodynamic pressure signal such as ePAD (estimated pulmonary arterial diastolic) pressure may be used as a parameter to monitor for controlling pulmonary capillary pressure. Step 804 may include determining whether the pulmonary capillary pressure measured in step 802 exceeds some threshold value, X, a high pressure setting, for example. If the monitored pulmonary capillary pressure does not exceed a high pressure set point X, the method continues to monitor and measure pulmonary capillary pressure at step 802. On the other hand, if the pulmonary capillary pressure exceeds the high pressure set point X, the method attempts to reduce pressure by raising the output of the left ventricle relative to the output of the right ventricle, as shown by step 806.

In some embodiments of the invention, a process of increasing the output of the left ventricle relative to that of the right ventricle may include determining certain initial conditions. For example, step 808 determines whether premature stimulation therapy delivery is being applied to the left ventricle. If premature stimulation therapy delivery is not being applied to the LV, step 812 may initiate premature stimulation therapy delivery to the LV to cause a PESP effect, and to thereby increase the output of the left ventricle. If it was determined in step 808 that premature stimulation therapy delivery was being applied to the LV, it may be useful in certain embodiments to next determine whether premature stimulation therapy delivery is being used in the RV, as shown by step 810. If step 810 determines that premature stimulation therapy delivery is not being applied to the RV, step 814 may adjust the ESI in the LV, for example. The ESI in the LV may be decreased in step 814 to increase the magnitude of the PESP effect in the LV, and to thereby increase the output of the left ventricle. If it was determined in step 810 that premature stimulation therapy delivery was being applied to the RV, step 815 may adjust either or both of the ESIs in the RV and/or LV in order to increase the magnitude of the PESP effect in the LV relative to that of the RV. Alternately, or additionally, step 816 may remove PESP from the RV (i.e., no premature, or extra, stimulus applied in the RV).

It should be noted that steps 808 through 816 described above roughly correspond to the steps described with reference to FIG. 6 above. Other combinations of these steps and/or sequential application of certain of these steps may be employed to achieve a similar result of increasing left ventricular output relative to right ventricular output. Such alternate combinations of steps to independently vary the respective impact or effect of premature stimulation therapy delivery to the RV and LV to control and/or equalize pulmonary capillary pressure. The foregoing and other advantages of the invention are contemplated and may become apparent to one of ordinary skill in the art with the benefit of these teachings.

Step 818 includes monitoring pulmonary capillary pressure to determine whether the actions taken in steps 808 through 816 have caused pulmonary capillary pressure to decrease. In step 820, if it is determined that pulmonary capillary pressure is not decreasing, the method restores prior and/or original therapy parameters, as shown by step 824. If, on the other hand, step 820 determines that pulmonary capillary pressure is decreasing, step 822 determines whether pulmonary capillary pressure has decreased below a predetermined set point, Y. If step 822 determines that pulmonary capillary pressure has not decreased below set point Y, then the method returns to step 806 and continues efforts to lower pulmonary capillary pressure by raising left ventricular output relative to right ventricular output. If pulmonary capillary pressure is determined to be below set point Y in step 822, the method returns to step 802 and continues to monitor pulmonary capillary pressure.

In certain embodiments of the invention (not shown in FIG. 8), a low pressure set point, Z, may be employed to determine if pulmonary capillary pressure has decreased to a level low enough to warrant taking active steps to increase pulmonary capillary pressure. Such actions would be similar to those described above, however the actions taken would tend to be in the opposite direction of those described above (i.e., the actions would attempt to increase the output of the right ventricle relative to that of the left ventricle).

Thus, embodiments of a METHOD AND SYSTEM FOR CONTROLLING PULMONARY CAPILLARY PRESSURE are disclosed. One skilled in the art will appreciate that the invention can be practiced with embodiments other than those disclosed. The disclosed embodiments are presented for purposes of illustration and not limitation, and the invention is limited only by the claims that follow.

The invention claimed is:

1. A method of treating pulmonary congestion episodes in a patient receiving pacing therapy in a first pacing mode, the method comprising:
    detecting a pulmonary congestion episode; and
    switching from the first pacing mode to a second pacing mode in response to the detected pulmonary congestion episode,
    wherein the second pacing mode increases a magnitude of a post extra-systolic potentiation (PESP) effect in a first ventricle (V1) relative to a magnitude of a post extra-systolic potentiation (PESP) effect in a second ventricle (V2).

2. A method according to claim 1 wherein a pulmonary congestion episode is detected when a monitored hemodynamic pressure signal exceeds a first hemodynamic pressure setting.

3. A method according to claim 2 further comprising switching back to the first pacing mode when the hemodynamic pressure signal decreases below a second hemodynamic pressure setting, the second hemodynamic pressure setting being less than the first hemodynamic pressure setting.

4. A method according to claim 2 wherein the hemodynamic pressure signal comprises an estimated pulmonary arterial diastolic (ePAD) pressure.

5. A non-transitory computer-readable medium programmed with instructions for performing a method of controlling pulmonary capillary pressure in an implantable medical device (IMD), the medium comprising instructions for causing a programmable processor to:
    monitor a hemodynamic pressure signal from a patient;
    detect a pulmonary congestion episode based on the monitored hemodynamic pressure signal; and
    switch from a first pacing mode to a second pacing mode in response to the detected episode,
    wherein the switch from the first pacing mode to the second pacing mode increases a magnitude of a post extra-systolic potentiation (PESP) effect in a first ventricle (V1) relative to a magnitude of a post extra-systolic potentiation (PESP) effect in a second ventricle (V2).

6. A medium according to claim 5 further comprising instructions to detect a pulmonary congestion episode when the monitored hemodynamic pressure signal exceeds a first hemodynamic pressure setting.

7. A medium according to claim 6 further comprising instructions to compare the hemodynamic pressure signal to a reference pressure measurement to account for changes in absolute pressure prior to switching to the second pacing mode.

8. A medium according to claim 7 further comprising instructions to adjust the first hemodynamic pressure setting based on changes in the reference pressure measurement.

9. A medium according to claim 6 further comprising instructions to switch back to the first pacing mode when the hemodynamic pressure parameter decreases below a second hemodynamic pressure setting, the second hemodynamic pressure setting being less than the first hemodynamic pressure setting.

10. A medium according to claim 6 further comprising instructions to switch back to the first pacing mode after a predetermined amount of time in the second pacing mode.

11. A medium according to claim 6 further comprising instructions to switch back to the first pacing mode if the hemodynamic pressure parameter continues to increase above the first hemodynamic pressure setting by a predetermined amount.

12. A medium according to claim 6 wherein the hemodynamic pressure parameter is estimated pulmonary arterial diastolic (ePAD) pressure.

13. A medium according to claim 5 further comprising instructions to enable a delivery of premature stimulation therapy to the first ventricle (V1) while operating in the second pacing mode.

14. A medium according to claim 5 further comprising instructions to disable a delivery of premature stimulation therapy delivery to the second ventricle (V2) while operating in the second pacing mode.

15. A medium according to claim 5 further comprising instructions to set the extra-stimulus interval (ESI) in the LV to a value in the second pacing mode which is lower than in the first pacing mode, and which is between 0-100 msec.

16. A medium according to claim 5 further comprising instructions to set the extra-stimulus interval (ESI) in the second ventricle (V2) to a value in the second pacing mode which is greater than in the first pacing mode, and which is between 0-100 msec.

17. A medium according to claim 5 further comprising instructions to include at least two of the following changes in the second pacing mode from the first pacing mode: enabling a post extrasystolic potentiation therapy in the first ventricle (V1) if not previously enabled, disabling a post extrasystolic potentiation therapy in the second ventricle (V2) if previously enabled, decreasing the extra-stimulus interval (ESI) in the first ventricle (V1), and increasing the extra-stimulus interval (ESI) in the second ventricle (V2).

18. A medium according to claim 5 further comprising instructions to include coupled pacing in the first and second pacing modes.

19. A medium according to claim 5 further comprising instructions to include paired pacing in the first and second pacing modes.

20. A medical device system comprising:
    an implantable medical device (IMD) and leads adapted to deliver pacing therapy to a patient;
    a sensor responsive to a signal representative of pulmonary capillary pressure in a patient and providing the signal to the IMD; and
    a processor programmed with instructions to:
    monitor the pulmonary capillary pressure signal from the patient;
    detect a pulmonary congestion episode based on the monitored pulmonary capillary pressure signal; and switch the IMD from a first pacing mode to a second pacing mode in response to the detected episode, wherein the switch from the first pacing mode to the second pacing mode increases a magnitude of a post extra-systolic potentiation (PESP) effect in a first ventricle (V1) relative to a magnitude of a post extra-systolic potentiation (PESP) effect in a second ventricle (V2).

21. A system according to claim 20 wherein the processor detects a pulmonary congestion episode when a monitored hemodynamic pressure signal exceeds a first hemodynamic pressure setting.

22. A system according to claim 21 wherein the processor switches back to the first pacing mode when the hemodynamic pressure signal decreases below a second hemodynamic pressure setting, the second hemodynamic pressure setting being less than the first hemodynamic pressure setting.

23. A system according to claim 21 wherein the hemodynamic pressure signal comprises an estimated pulmonary arterial diastolic (ePAD) pressure.

24. A system according to claim 20 wherein the processor switches back to the first pacing mode after a predetermined amount of time in the second pacing mode.

25. A system according to claim 20 wherein the processor enables a delivery of premature stimulation therapy to the first ventricle (V1) while operating in the second pacing mode.

26. A system according to claim 20 wherein the processor detects a delivery of premature stimulation therapy delivery to the second ventricle (V2) while operating in the second pacing mode.

27. A system according to claim 20 wherein the processor sets the extra-stimulus interval (ESI) in the LV to a value in the second pacing mode which is lower than in the first pacing mode, and which is between 0-100 msec.

28. A system according to claim 20 wherein the processor sets the extra-stimulus interval (ESI) in the second ventricle (V2) to a value in the second pacing mode which is greater than in the first pacing mode, and which is between 0-100 msec.

29. A medium according to claim 20 wherein the processor includes at least two of the following changes in the second pacing mode from the first pacing mode: enabling a post extrasystolic potentiation therapy in the first ventricle (V1) if not previously enabled, disabling a post extrasystolic potentiation therapy in the second ventricle (V2) if previously enabled, decreasing the extra-stimulus interval (ESI) in the first ventricle (V1), and increasing the extra-stimulus interval (ESI) in the second ventricle (V2).

30. A system according to claim 20 wherein the processor includes coupled pacing in the first and second pacing modes.

31. A system according to claim 20 wherein the processor includes paired pacing in the first and second pacing modes.

* * * * *